US00PP23907P2

(12) United States Plant Patent
Hansen

(10) Patent No.: US PP23,907 P2
(45) Date of Patent: Sep. 17, 2013

(54) ***BAPTISIA* PLANT NAMED 'CHERRIES JUBILEE'**

(50) Latin Name: *Baptisia×variicolor*
Varietal Denomination: Cherries Jubilee

(75) Inventor: Hans Andrew Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 84 days.

(21) Appl. No.: 13/374,344

(22) Filed: Dec. 22, 2011

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Penny J. Aguirre

(57) ABSTRACT

A new cultivar of interspecific *Baptisia*, 'Cherries Jubilee', characterized by its bi-color flowers that are maroon with a yellow keel held on erect flower stems, its densely branched, uniform and upright plant habit, its vigorous growth rate and its hardiness to U.S.D.A. Zones 4 to 8.

2 Drawing Sheets

Botanical classification: *Baptisia×variicolor.*
Cultivar designation: 'Cherries Jubilee'.

BACKGROUND OF THE INVENTION

The present invention relates to a new and distinct cultivar of hybrid *Baptisia* plant, botanically known as *Baptisia×variicolor* 'Cherries Jubilee' and will be referred to hereafter by its cultivar name, 'Cherries Jubilee'. The new cultivar represents a new false indigo, an herbaceous perennial grown for garden and landscape use.

The new invention arose from an ongoing controlled breeding program in Waseca, Minn. that was established by the Inventor in 1998 using superior selections of numerous species of *Baptisia* with the goal of developing unique color forms and plant habits of *Baptisia* suited for general garden and landscape use.

'Cherries Jubilee' was derived from an F1 cross made in 2003 (cross no. 03) between an unnamed plant of *Baptisia sphaerocarpa* as the female parent and an unnamed plant selection of *Baptisia minor* as the male parent. 'Cherries Jubilee' was selected in 2007 as a single unique plant amongst the progeny of the cross.

Asexual reproduction of the new cultivar was first accomplished by stem cuttings in early June of 2008 in Zeeland, Mich. under the direction of the Inventor. The characteristics of this cultivar have been determined to be stable and are reproduced true to type in successive generations.

SUMMARY OF THE INVENTION

The following traits have been repeatedly observed and represent the characteristics of the new cultivar as observed for five years in Waseca, Minn. These attributes in combination distinguish 'Cherries Jubilee' from other varieties of *Baptisia* known to the Inventor.

1. 'Cherries Jubilee' exhibits flowers that are bi-color; maroon in color with a yellow keel, a characteristic that has not been observed in any species or hybrid known to the Inventor.
2. 'Cherries Jubilee' exhibits blue-green foliage.

3. 'Cherries Jubilee' exhibits a vigorous growth habit.
4. 'Cherries Jubilee' has an upright and uniform plant habit.
5. 'Cherries Jubilee' produces abundant flower stems produced above the mound of foliage.
6. 'Cherries Jubilee' is hardy in U.S.D.A. Zones 4 to 8.

In comparison to the female parent, an unnamed plant of *Baptisia sphaerocarpa*, 'Cherries Jubilee' has maroon flowers with a yellow keel whereas *Baptisia sphaerocarpa* has yellow flowers, 'Cherries Jubilee' also has a more upright habit, larger flowers, and longer inflorescences. In comparison to the male parent, an unnamed plant of *Baptisia minor*, 'Cherries Jubilee' has maroon flowers with a yellow keep whereas *Baptisia minor* has blue-violet flowers, 'Cherries Jubilee' also differs in having a greater quantity of flower spikes and in maturing to a more compact size. 'Cherries Jubilee' has seed pods that are intermediate in characteristics between the two parents, but the seed pods are more similar to the female parent in shape, color, and thickness. The closest comparison cultivar is *Baptisia* 'Twilite' (U.S. Plant Pat. No. 19,001). 'Twilite' is also an interspecific hybrid, however it differs in having violet-lavender colored flowers with a yellow keel. 'Cherries Jubilee' can also be compared to 'Chocolate Chip', an additional interspecific hybrid, however 'Chocolate Chip' has inflorescences that arch at a 45° angle midway at the bloom sequence, has a more open plant habit and form, and a flower color that is darker and closer to purple-brown.

BRIEF DESCRIPTION OF THE DRAWINGS

The accompanying colored photographs illustrate the overall appearance and distinct characteristics of the new *Baptisia*. The photographs were taken of plants and plant parts of a plant five years in age as grown outdoors in Waseca, Minn.

The photograph in FIG. 1 is a view of a plant of 'Cherries Jubilee' in bloom and illustrates the overall general plant-habit and flower aspect.

Figure 1:
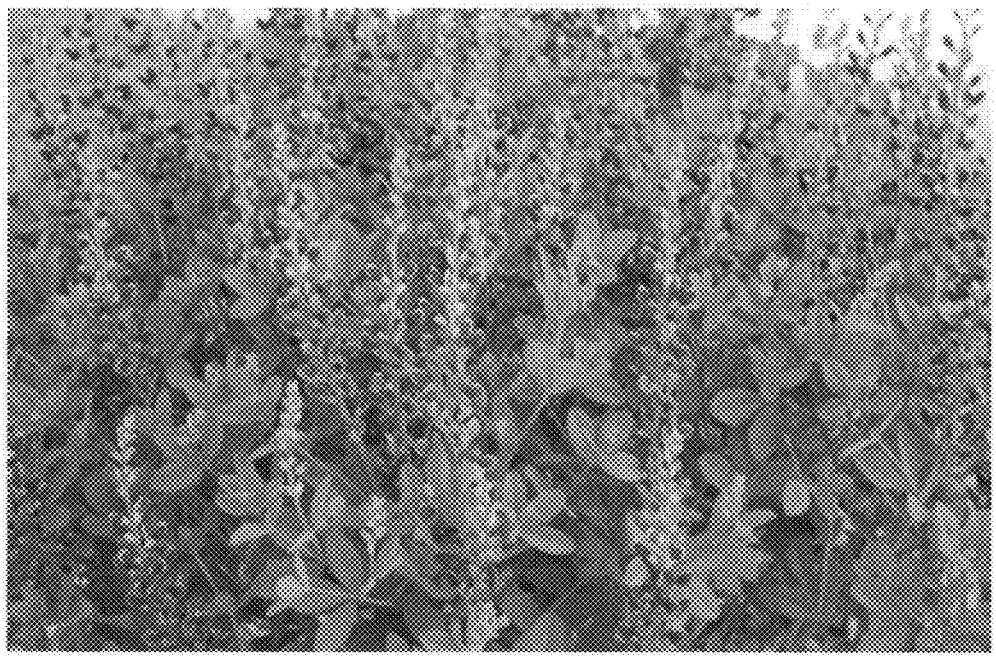
Figure 2:
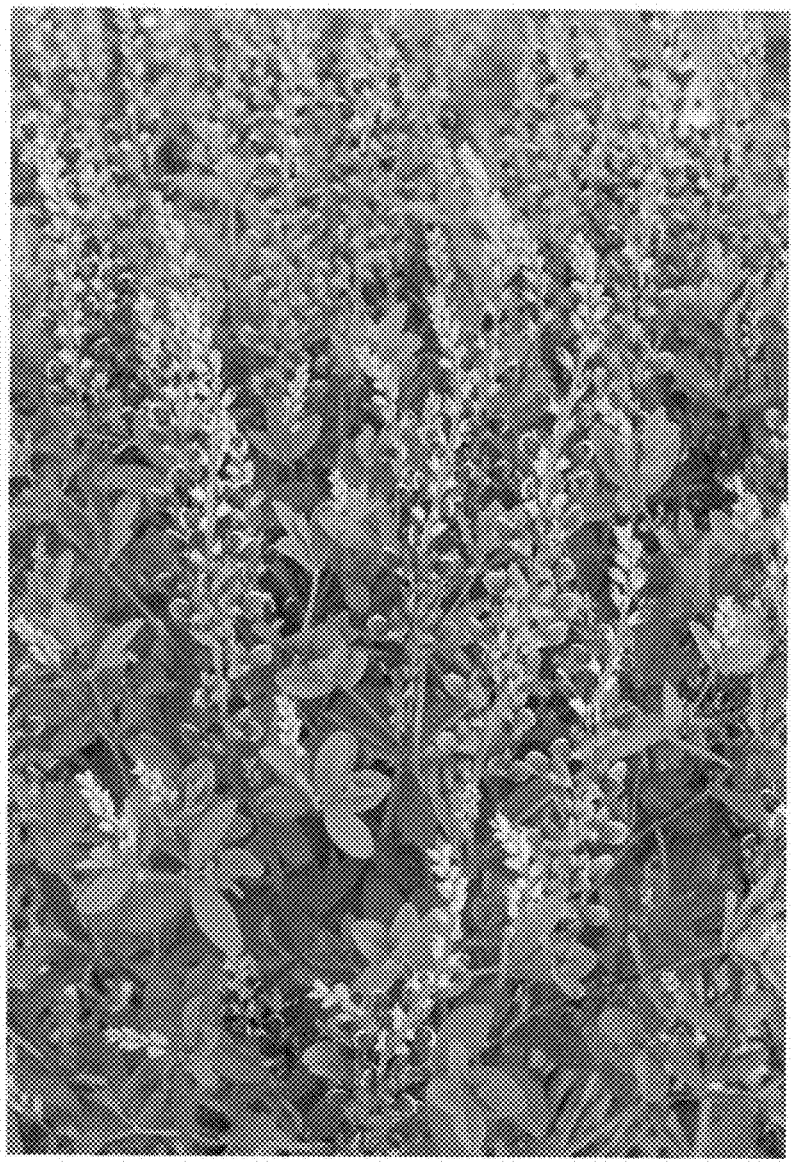

The photograph in FIG. 2 provides a view of the inflorescences of 'Cherries Jubilee' and illustrates the flower form and color early in the flower sequence. The colors in the photographs may differ slightly from the color values cited in the detailed botanical description, which accurately describe the colors of the new Baptisia.

DETAILED BOTANICAL DESCRIPTION OF THE PLANT

The following is a detailed description of 5 year-old plants of the new cultivar as grown outdoors in a trial plot in Waseca, Minn. The phenotype of the new cultivar may vary with variations in environmental, climatic, and cultural conditions, as it has not been tested under all possible environmental conditions. The color determination is in accordance with The 2001 R.H.S. Colour Chart of the Royal Horticultural Society, London, England, except where general color terms of ordinary dictionary significance are used.

General description:

*Blooming period*.—Early June through late June in Waseca, Minn. (June 5-June 28).

*Plant habit*.—Densely foliaged, vase-shaped.

*Height and spread*.—Reaches 84 cm width and 87 cm in height.

*Hardiness*.—U.S.D.A. Zones 4 to 8.

*Culture*.—Prefers well-drained to medium moist soils in full sun, tolerant to lean soils and drought.

*Diseases and pests*.—No susceptibility to diseases or pests has been observed.

*Root description*.—Deep rooted, fibrous.

Growth and propagation:

*Propagation*.—Stem cuttings, tissue culture is also possible.

*Growth rate*.—Vigorous.

Stem description:

*Branch habit*.—Very densely branched; average of 40 branches with an average of 3 secondary branches, and 2 tertiary branches per secondary branch.

*Stem size*.—Main stem; average of 56 cm (including peduncle) in length and 6 mm in width (7 mm at base), secondary; average of 25 cm in length and 3 mm, tertiary; an average of 13 cm in length and 2 mm in width.

*Stem shape*.—Oval.

*Stem color*.—144A to 144B.

*Stem surface*.—Hairless, satiny but slightly glaucous, fine vertical ridges.

*Stem aspect*.—Upright.

*Stem strength*.—Strong.

Foliage description:

*Leaf shape*.—Fan-shaped in overall outline.

*Leaf division*.—3-palmate.

*Leaf internode*.—Foliage begins 33 cm from base, an average of 7.5 cm on main stem and 6.5 on secondary branches.

*Leaf size*.—About 6 cm in length and 8 cm in width when mature.

*Leaf quantity*.—About 27 per stem.

*Leaflet shape*.—Oblanceolate.

*Leaflet base*.—Cuneate.

*Leaflet apex*.—Retuse.

*Leaflet venation*.—Pinnate pattern, not conspicuous, color matches leaflet color on the upper and lower surface with the mid rib of lower surface 146D.

*Leaflet margins*—Entire.

*Leaf attachment*.—Petiolate.

*Leaf arrangement*.—Alternate.

*Leaflet surface*.—Glabrous and slightly glaucous on upper and lower surface with lower surface more glaucous.

*Leaflet color*.—Newly expanded upper and lower surface; color between 144A and 137C, mature; upper and lower surface N138B.

*Leaflet size*.—An average of 6 cm in length and 2.2 cm in width.

*Petioles*.—Average of 5 mm in length and 2 mm in width, clasping to stem at mature nodes, 146B in color, surface is glabrous and satiny.

*Stipules*.—Narrowly lanceolate in shape, not present on all stems, slightly reflexed to horizontal to stem, base is truncate to stem, apex is apiculate, average of 2.3 cm in length and 5 mm in width on mature leaves, color is 137C to 137D on upper surface and 138A to 138B on lower surface.

Flower description:

*Inflorescence type*.—Terminal racemes of pea-like flowers on main with smaller racemes on secondary branches, blooms from the base to the apex.

*Inflorescence size*.—Average of 22 cm in length and 4.2 cm in width in mid section.

*Lastingness of inflorescence*.—About 23 days.

*Flower size*.—About 2.6 cm in depth and about 1.7 cm in diameter.

*Flower fragrance*.—Faint.

*Flower number per inflorescence*.—About 32.

*Peduncle*.—Oval in shape, up to 26 cm in length and an average of 2.3 mm in width, 144B heavily suffused with 197A in color, surface is glabrous, satiny and slightly glaucous, flower internode length averages about 5 mm.

*Petiole*.—About 4 mm in length, about 1.5 mm in width, oval in shape, 144B heavily suffused with 197A in color, glabrous and satiny surface.

*Flower buds*.—Kidney-shaped, about 2.2 cm in length and 9 mm in width, color of petal 145A and heavily suffused with 187A to 187B with the basal portion 145A with exposed keel portion 145A, calyx portion same as open flowers.

*Flower type*.—Papilionaceous, held at about a 45° angle.

*Calyx*.—Campanulate, about 8 mm in length and 6 mm in diameter, surface is glabrous and satiny, 144B in color suffused at base with N200B, persistent.

*Sepals*.—5, fused with the exception of apex of each, free portion is triangular in shape 2 mm in width and 3 mm in depth with an acute apex, 144B in color suffused at base with N200B.

*Corolla features*.—Papilionaceous (4 segments) with a keel, a banner and 2 lateral wings, lateral wings; obelliptic in shape, flared to expose keel, about 2.4 cm in length and 1 cm in width, color on outer surface and inner surface 8A and heavily suffused with 187A to 187B with the basal portion 8A, rounded apex, oblique base, keel; only partially visible, comprised of 2 segments surrounding reproductive organs, oblong (slightly oblique) in shape with rounded apex and oblique base, 2.2 cm in length and 1 cm in width, upper surface and lower surface are 1A in color becoming 1C at base, banner; orbicular in shape and partially reflexed, about 1.7 cm in length and 1 cm in width when reflexed, upper and lower surface is 8A and heavily suffused with N186B with the basal portion 8A, midrib 145A with spots of 187A, apex is rounded with a single notch, surface is glabrous and margins are on all sections.

*Receptacle*.—Disk-shaped, gelatinous, 137A in color, about 3 mm in diameter and 1.2 mm in depth.

Reproductive organs:

*Gynoecium*.—1 Pistil, about 2 cm in length, 1.5 mm in width; style is 144B in color and 1 cm in length; stigma minute, too small to read color, ovary is superior with a stipe, 138B in color, 8.5 mm in length and 1.7 mm in width; stipe is 138A in color, 5 mm in length and 1 mm in width.

*Androcoecium*.—10 stamens, not united, 2.2 cm in length and 1 mm in width; filament is 2 cm in length, 1 mm in width and 145C in color; anther is dorsifixed, many oval shaped, about 1 mm in length and width and 162B in color, pollen is abundant 14B.

*Fruit*.—An inflated pod, technically a legume, 15 to 38 produced per inflorescence (open-pollinated), globose in shape, 1.8 cm in length and 1.5 to 1.7 cm in width; each with a short beak approximately 2 mm in length stipe about 8 to 9 mm in length 1 mm in width, color of outer surface when mature in September a blend of 201A and 202A color of inner surface 199A, interior surface glossy, outer surface rough, walls 2 mm in thickness, seed; 1 to 3 per fruit (open pollinated) 164B to 165B in color, oval with the hilum side more or less straight, seed compressed to flattish, 4 mm in length, 3 mm wide×1.5 mm in thickness.

It is claimed:

1. A new and distinct cultivar of *Baptisia* plant named 'Cherries Jubilee' as herein illustrated and described.

* * * * *